United States Patent
Di Teodoro et al.

(10) Patent No.: US 6,706,930 B2
(45) Date of Patent: Mar. 16, 2004

(54) PROCESS FOR THE PREPARATION OF HALOGENATED HYDROXYDIPHENYL COMPOUNDS

(75) Inventors: Armando Di Teodoro, Rheinfelden (DE); Werner Hölzl, Eschentzwiller (FR); Dieter Reinehr, Kandern (DE); Rudolf Zink, Therwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/275,022

(22) PCT Filed: Apr. 26, 2001

(86) PCT No.: PCT/EP01/04710

§ 371 (c)(1),
(2), (4) Date: Oct. 31, 2002

(87) PCT Pub. No.: WO01/83418

PCT Pub. Date: Nov. 8, 2001

(65) Prior Publication Data

US 2003/0163005 A1 Aug. 28, 2003

(30) Foreign Application Priority Data

May 4, 2000 (EP) ............................................. 00810382

(51) Int. Cl.⁷ .............................................. C07C 41/00
(52) U.S. Cl. ...................... 568/639; 568/628; 568/637; 568/638
(58) Field of Search ................ 568/639, 637, 568/628, 638

(56) References Cited

U.S. PATENT DOCUMENTS

| 6,215,029 B1 | 4/2001 | Burckhardt et al. ........ 568/639 |
| 2002/0128522 A1 | 9/2002 | Teodoro et al. ............. 568/637 |

FOREIGN PATENT DOCUMENTS

| EP | 0857711 | 9/1998 |
| WO | 99/10310 | 3/1999 |

*Primary Examiner*—Johann Richter
*Assistant Examiner*—Elvis O. Price
(74) *Attorney, Agent, or Firm*—Kevin T. Mansfield

(57) ABSTRACT

There is described a process for the preparation of halogenated hydroxydiphenyl compounds of formula (1) by acylation of a halogenated benzene compound (first stage), etherification of the acylated compound with a halogenated phenol compound, which is not further substituted in the ortho-position (second stage), oxidation of the etherified compound (third stage) and hydrolysis of the oxidized compound in a fourth stage, wherein the reaction of the second stage is carried out in the presence of $K_2CO_3$ and any desired copper catalyst, where $K_2CO_3$ is used in a concentration of from 0.5 to 30 mol, based on the phenol compound employed of formula (6), according to the reaction scheme (I) in which $R_1$ and $R_2$ independently of one another are F, Cl or Br; $R_3$ and $R_4$ independently of one another are hydrogen; or $C_1$–$C_4$alkyl; m is 1 to 3; and n is 1 or 2. The compounds of formula (1) are used for protecting organic materials and articles from microorganisms.

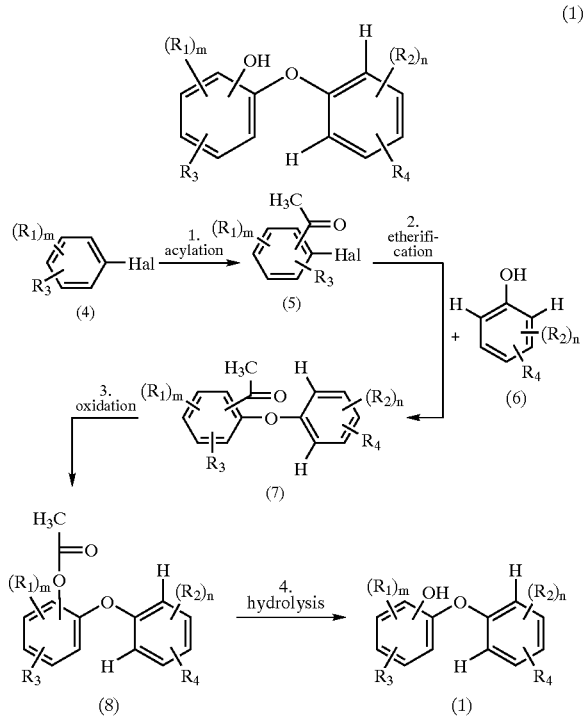

11 Claims, No Drawings

PROCESS FOR THE PREPARATION OF HALOGENATED HYDROXYDIPHENYL COMPOUNDS

This application is a 371 of PCT/EP01/04210, filed Apr. 26, 2001.

The present invention relates to the preparation of halogenated hydroxydiphenyl compounds of the formula

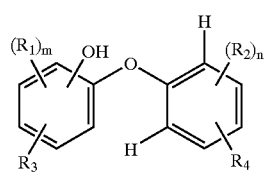
(1)

in which
$R_1$ and $R_2$ independently of one another are F, Cl or Br;
$R_3$ and $R_4$ independently of one another are hydrogen; or $C_1$–$C_4$alkyl;
m is 1 to 3; and
n is 1 or 2;
and to the use of these compounds as disinfectants for protecting organic materials from microorganisms.

WO 99/10310 discloses a four-stage process for the preparation of 2,4,4'-trichloro-2'-hydroxydiphenyl ether (triclosan) by acylation of a halobenzene compound (first stage), etherification of the acylated compound using a halogenated phenol compound in an Ullmann-analogous reaction (second stage), Baeyer-Villiger oxidation of the etherified compound (third stage) and subsequent hydrolysis.

However, the yields in this process are moderate, in particular yields of <50% are achieved in the 2$^{nd}$ reaction stage (Ullmann condensation).

Surprisingly, it has been found that significantly higher yields can be achieved for the second reaction stage if halogenated phenol compounds which are not further substituted in the ortho position are used as starting compounds for the Ullmann condensation.

The present invention therefore relates to a four-stage process for the preparation of halogenated hydroxydiphenyl compounds, which are not further substituted in the 2'- and 6'-position, of the formula (1), in which in the first stage a halogenated benzene compound is acylated, in the second stage the acylated compound is etherified using a halogenated phenol compound which is not further substituted in the ortho-position, in a third stage the etherified compound is oxidized and in the fourth stage the oxidized compound is hydrolysed, wherein the reaction of the second stage is carried out in the presence of $K_2CO_3$ and any desired copper catalyst, where $K_2CO_3$ is used in a concentration of from 0.5 to 3 mol, based on the phenol compound employed of the formula (6), according to the following reaction scheme:

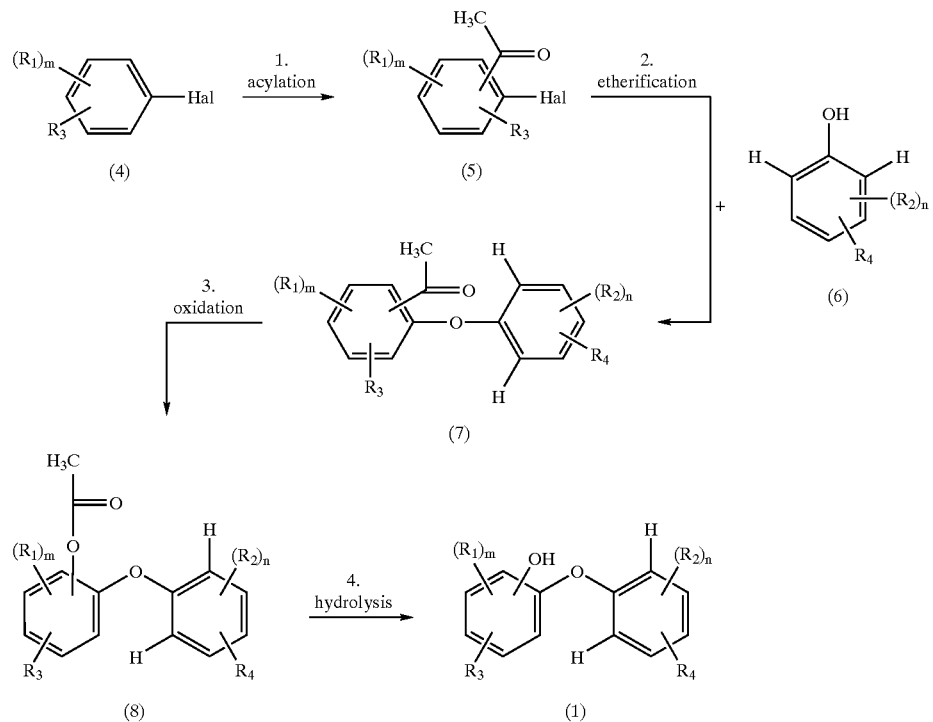

In the above scheme, $R_1$, $R_2$, $R_3$, $R_4$, m and n are as indicated in formula (1).

In the first reaction step (acylation reaction), compounds of the formula (5) are prepared. Usually, this reaction is carried out in the presence of a Lewis acid, e.g. aluminium halide, in particular aluminium chloride. The Lewis acid is in this case employed in a 1 to 3, preferably 1.25 to 2, molar amount, based on the halogenated compound of the formula (5). A possible acylating reagent for this reaction is an acyl halide, in particular acetyl chloride.

$C_1$–$C_4$alkyl is preferably a straight-chain or branched alkyl radical, e.g. methyl, ethyl, n-propyl, isopropyl, n-butyl, sec-butyl or tert-butyl.

The Lewis acid and acylating reagent are preferably employed in equimolar amounts. The reaction is carried out in the solvents customary for Friedel-Crafts reactions, e.g.

nitrobenzene, dichlorobenzene, methylene chloride or ethylene chloride. The reaction time for this reaction stage plays a minor part and can vary within wide bounds, from, for example, 1 to 18 hours.

In the second reaction stage, the compounds of the formula (7) are prepared. The etherification of the free OH group of the halogenated phenol compound of the formula (6) is carried out in alkaline medium using $K_2CO_3$, and in the presence of any copper catalyst, for example metallic copper, copper(I) and copper(II) oxides, copper halides and copper acetates or $CuCO_3 \times Cu(OH)_2$ and an inert organic solvent, e.g. toluene or a xylene isomer mixture. The reaction can also be carried out, however, in the presence of polar solvents, for example DMF or DMSO.

The reaction times for this reaction step are usually 1 to 24 hours, preferably 2 to 10 hours; the temperature ranges from 80 to 250° C., preferably 100 to 170° C.

The base ($K_2CO_3$) is used in concentrations of preferably from 0.8 to 2 mol per mole and very particularly 0.9 to 1.1 mol per mole, based on the phenol compound employed.

The phenol compound of the formula (6) is preferably employed in a definite excess.

In the third reaction stage (oxidation), compounds of the formula (8) are prepared.

The oxidation of the acyl compound of the formula (7) to the compound of the formula (8) (Baeyer-Villiger oxidation) can be carried out using various oxidizing agents. Suitable oxidizing agents are, for example:

a mixture of dilute peracetic acid and acetic anhydride in the presence of a catalytic amount of perchloric acid;

m-chloroperbenzoic acid (MCPBA) in water;

diperoxydodecanedioic acid (DPDDA);

a mixture of dilute peracetic acid and acetic anhydride and sulfuric acid;

perbenzoic acid (PBA)

a mixture of sodium borate and trifluoroacetic acid;

a mixture of formic acid, hydrogen peroxide, acetic anhydride, phosphorus pentoxide and acetic acid;

a mixture of acetic acid, hydrogen peroxide, acetic anhydride and phosphorus pentoxide;

a mixture of hydrogen peroxide/sulfuric acid/acetic acid;

a mixture of $K_2S_2O_8$, sulfuric acid and a 1:1 water/methanol mixture;

a mixture of acetic acid and the potassium salt of monoperoxymaleic acid;

a mixture of trichloromethylene, the potassium salt of monoperoxymaleic acid and sodium hydrogen sulfate;

a mixture of maleic anhydride, acetic anhydride, hydrogen peroxide and trichloromethane;

a mixture of maleic anhydride, a urea-hydrogen peroxide complex and acetic acid;

magnesium monoperphthalate;

a mixture of acetic anhydride, sulfuric acid and $H_2O_2$;

a mixture of dichloroacetic acid and $H_2O_2$.

m-Chloroperbenzoic acid (MCPBA) or a mixture of hydrogen peroxide/sulfuric acid/acetic acid is preferably used for the oxidation.

If desired, a commercially available wetting agent can additionally be added to the oxidizing agent. The reaction times lie in a wide range and range from about 0.5 to about 15 hours, preferably 1 to 8 hours. The reaction temperature ranges from −20 to about 100° C., preferably from 0 to about 85° C.

The subsequent hydrolysis to give the desired halohydroxydiphenyl ether of the formula (1) proceeds quantitatively in the acidic or alkaline medium.

The process according to the invention preferably relates to the preparation of halohydroxydiphenyl compounds of the formula (1), in which $R_1$ and $R_2$ are Cl.

Very particularly preferred compounds of the formula (1) have the formula

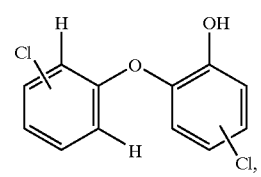

(9)

and in particular the formula

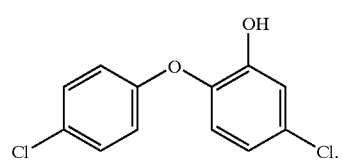

(10)

The halogenated hydroxydiphenyl compounds prepared according to the invention are insoluble in water, but soluble in dilute sodium hydroxide and potassium hydroxide solution and in virtually all organic solvents. Owing to these solubility requirements, their applicability for the control of microorganisms, in particular of bacteria, and as disinfectants for protecting organic materials and articles from attack by microorganisms is very versatile. Thus they can be applied to these in diluted or undiluted form, for example, together with wetting or dispersing agents, e.g. as soap or syndet solutions for the disinfection and cleaning of human skin and hands, of hard articles and in dental hygiene compositions.

The following examples illustrate the invention without restricting it thereto.

PREPARATION EXAMPLES

Example 1

Preparation of 2,5-dichloroacetophenone (First Reaction Stage)

Reaction Scheme:

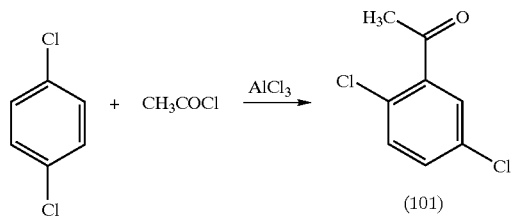

(101)

147 g (1.0 mol) of p-dichlorobenzene are completely melted at 60° C. in an apparatus having an attached dropping funnel, stirrer and reflux condenser. 120 g (0.9 mol) of anhydrous $AlCl_3$ are added to the melt. 39.3 g (0.5 mol) of acetyl chloride are then added dropwise to the readily stirrable suspension at 60° C. in the course of about 1 hour, a clear solution slowly resulting. After heating to 110° C., the mixture is stirred at this temperature for 7 hours. After cooling to room temperature, the brown reaction mass is hydrolysed by cautious decantation onto a mixture of 200 ml of water and 200 g of ice. The temperature of the mixture is kept between 30 and 40° C. during the hydrolysis by external cooling. After separation of the phases, the lower, organic phase is washed with 400 ml of water and, after fresh phase separation, subjected to fractional distillation. The aqueous phases are discarded.

Yield: 66 g of 2,5-dichloroacetophenone (70% of theory, based on acetyl chloride)

Example 2

Preparation of 1-(5-chloro-2-(2,4-dichlorophenyl) phenylethanone (Second Reaction Stage)

Reaction Scheme:

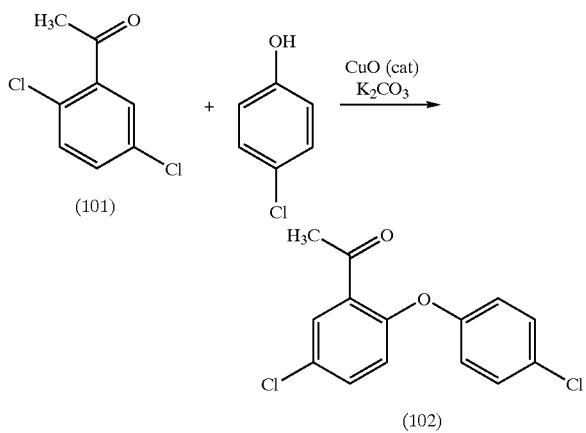

164.4 g of $K_2CO_3$ (1.03 mol), 0.86 g of copper(II) oxide and 600 g of xylene isomer mixture are initially introduced and 132.5 g of 4-chlorophenol and 189.1 g of 2,5-dichloroacetophenone are introduced with stirring. The grey suspension is heated to reflux at 144° C. and 8 g of water are distilled off in a water separator. After a residence time of 2.5 h at 145° C., the reaction mass is cooled to 80° C., 500 g of water are added and the mixture is stirred for 15 min. Phase separation is then awaited in a separating funnel. The lower aqueous phase is separated off (670 g). The conversion in the remaining organic phase (desalted reaction mass; 921 g) is determined by means of HPLC.

Yield: 257.0 g of the compound of the formula (102) (91.3% of theory).

Example 3

Preparation of 1-(5-chloro-2-(2,4-dichlorophenoxy) phenyl)ethanone (2nd Reaction Stage) Using Basic Copper Carbonate as the Catalyst The procedure is as described in Example 2, with the difference that instead of copper(II) oxide, basic copper carbonate ($CuCO_3 \times Cu(OH)_2$) is employed. The yield is 260.7 g of the compound of the formula (102); (92.6% of theory).

Example 4

Preparation of 5-chloro-2-(4-chlorophenoxy)phenol (Third and Fourth Reaction Stage)

Reaction Scheme:

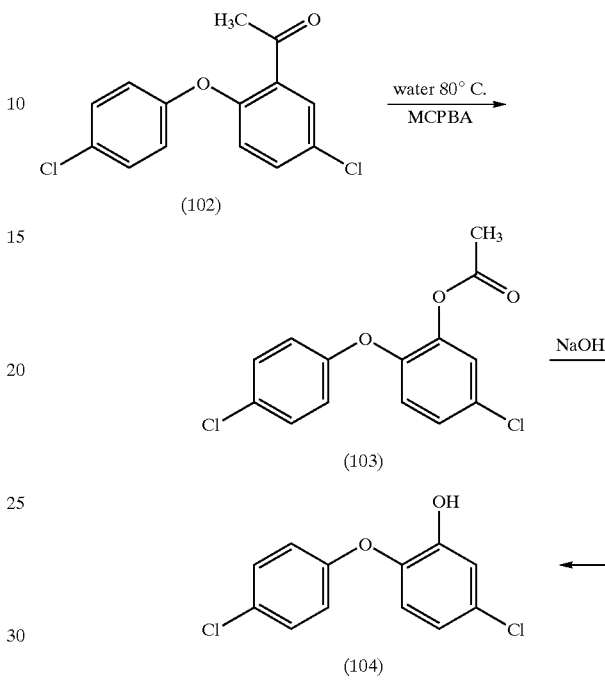

14 g of the acetyl compound of the formula (102) are suspended in 100 ml of deionized water at 20° C. using a wetting agent. 29 g of 70% 3-chloroperbenzoic acid (MCPBA) are scattered in and the mixture is heated with stirring. A resin/water phase is formed from 52° C.; the mixture is heated to about 80° C. and kept at this temperature for 7 hours.

It is treated with 0.5 g of sodium hydrogen sulfite to destroy excess peroxide. Two clear phases are obtained by addition of 50 ml of xylene isomer mixture and 9 g of 10N NaOH. The water phase having a pH of about 12 is separated off; the solvent phase comprising the compound of the formula (103) is washed with water until neutral.

To hydrolyse the ester, the xylene phase is treated with 24 g of 10% NaOH and stirred under reflux (about 95° C.) for 5 hours. The xylene phase is then separated off and the pale brown water phase is adjusted to a pH of about 3 using 4 g of 34% hydrochloric acid at 25° C. In the course of this, the product precipitates in sandy, beige-coloured form and, after filtration, can be thoroughly washed with water on the suction filter. After drying, 5 g of the crude product of the formula (104) having a melting point of 73 to 74° C. are obtained.

After recrystallization from petroleum ether 80/110, the pure substance is obtained in colourless crystals having a melting point of 74 to 74.5° C.

Example 5

Preparation of 5-chloro-2-(4-chlorophenoxy)phenol (Third and Fourth Reaction Stage)

a) Preparation of the Baeyer-Villiger Reaction (=BV Reagent)

300 g of anhydrous acetic acid are initially introduced, 102 g of 96% sulfuric acid are metered in (internal temperature <30° C.).

106.2 g of 50% hydrogen peroxide solution are metered in, the internal temperature being maintained at <20° C.

The mixture is then stirred for a further hour at 20° C.

b) Preparation of the Baeyer-Villiger Initial Mixture (=BV Initial Mixture)

450 g of anhydrous acetic acid are initially introduced with cooling, 440 g of 96% sulfuric acid are metered in (internal temperature <30° C.), 281.1 g of crystalline 2-acetyl-4,4'-dichlorophenyl ether are introduced at an internal temperature of 20° C.

c) Baeyer-Villiger Reaction

BV reagent is metered into the BV initial mixture in the course of 4 hours (internal temperature 30° C.).

The reaction is then kept at an internal temperature of 40° C. for 2 hours and at an internal temperature of 50° C. for 0.5 hours.

d) Work-Up

The work-up is carried out according to the customary methods.

623 g of 2-OH-4,4'-DCDPE are obtained as a 30% solution in 1,2-PG. This corresponds to 187 g of 100% strength of 2-OH-4,4'-DCDPE (73% of theory).

What is claimed is:

1. A process for the preparation of halogenated hydroxydiphenyl compounds, which are not substituted in the 2'- and 6'-position, of the formula

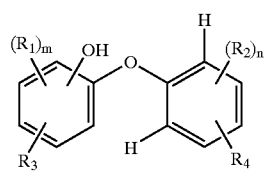
(1)

by acylation of a halogenated benzene compound (first stage), etherification of the acylated compound with a halogenated phenol compound which is not further substituted in the ortho-position (second stage), oxidation of the etherified compound (third stage) and hydrolysis of the oxidized compound in a fourth stage, wherein the reaction of the second stage is carried out in the presence of $K_2CO_3$ and any desired copper catalyst, where $K_2CO_3$ is used in a concentration of from 0.5 to 3 mol, based on the phenol compound employed of the formula (6) according to the following reaction scheme:

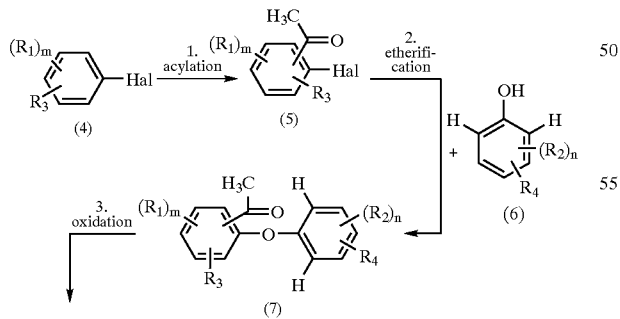

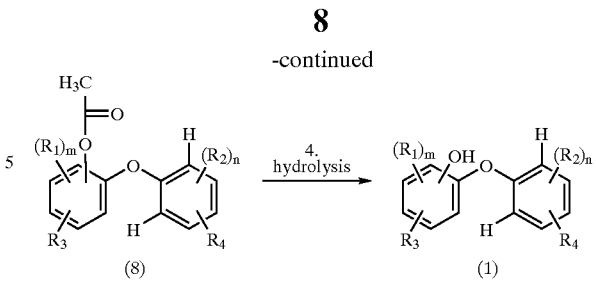

where
$R_1$ and $R_2$ independently of one another are F, Cl or Br;
$R_3$ and $R_4$ independently of one another are hydrogen; or $C_1$–$C_4$alkyl;
m is 1 to 3; and
n is 1 or 2.

2. A process according to claim 1, wherein the acylation reaction (first stage) is carried out in the presence of a Lewis acid.

3. A process according to claim 1, wherein an acyl halide is used for the acylation reaction.

4. A process according to claim 1, wherein the base $K_2CO_3$, is employed in a concentration of from 0.8 to 2 mol, based on the phenol compound employed.

5. A process according to claim 4, wherein the base is employed in a concentration of from 0.9 to 1.1 mol, based on the phenol compound employed.

6. A process according to claim 1, wherein the oxidation ($3^{rd}$ reaction stage) is carried out in the presence of percarboxylic acids.

7. A process according to claim 6, wherein the oxidation is carried out in the presence of n MCPBA (m-chloroperbenzoic acid) or peracetic acid.

8. A process according to claim 1, wherein the oxidation ($3^{rd}$ reaction stage) is carried out in the presence of a mixture of hydrogen peroxide/sulfuric acid/acetic acid.

9. A process according to claim 1, which relates to the preparation of compounds of the formula (1) in which $R_1$ and $R_2$ are Cl.

10. A process according to claim 1, which relates to the preparation of compounds of the formula

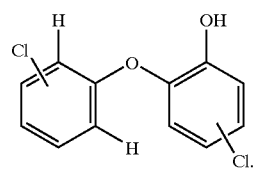
(9)

11. A process according to claim 1, which relates to the preparation of the compounds of the formula

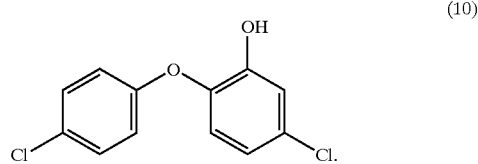
(10)

* * * * *